United States Patent [19]
Clark et al.

[11] Patent Number: 4,675,285
[45] Date of Patent: Jun. 23, 1987

[54] METHOD FOR IDENTIFICATION AND ISOLATION OF DNA ENCODING A DESIRED PROTEIN

[75] Inventors: Steven C. Clark, Winchester; Randal J. Kaufman, Boston; Gordon G. Wong, Cambridge, all of Mass.

[73] Assignee: Genetics Institute, Inc., Cambridge, Mass.

[21] Appl. No.: 652,316

[22] Filed: Sep. 19, 1984

[51] Int. Cl.$^4$ .................. C12Q 1/68; C12P 21/00; C12N 15/00; C12N 5/00
[52] U.S. Cl. .......................... 435/6; 435/68; 435/172.3; 435/240; 435/317; 935/78; 935/11; 935/56
[58] Field of Search .................. 435/6, 68, 91, 172.3, 435/240, 241, 317, 948, 255, 253; 935/2, 11, 19, 21, 28, 29, 42, 43, 47, 48, 56, 60, 69, 70, 72, 78, 79

[56] References Cited

U.S. PATENT DOCUMENTS 4,446,235  5/1984  Seeburg ............................ 935/78 X
4,517,294  5/1985  Bock et al. ..................... 435/172.3 X
4,520,106  5/1985  Kado ................................ 435/172.3

OTHER PUBLICATIONS

Okayama et al., Mol. Cell Biol. vol. 3, No. 2, pp. 280–289 (1983).
Gray et al., Nature 295 pp. 503–508 (1982).
Yokoto et al., Proc. Natl. Sci. USA, vol. 81, pp. 1070–1074 (1984).

Primary Examiner—Esther M. Kepplinger
Assistant Examiner—Jeremy Jay
Attorney, Agent, or Firm—Dike, Bronstein, Roberts, Cushman & Pfund

[57] ABSTRACT

A method for identifying and isolating clones containing DNA coding for a desired protein is described. DNA prepared from a cell that expresses the desired protein is inserted into an isolation expression vector having means for replication (as a means of producing DNA) and a suitable promoter for expression of said DNA in a predetermined mammalian host cell as well as means for replication in a bacterial cell. The transient expression vector is then inserted into a bacterial cell for replication of the DNA. Pools of DNA, prepared from a predetermined number of bacterial clones so that the nucleic acids (DNA and RNA) is substantially free of other bacterial contaminants are transfected or microinjected into mammalian host cells and conditioned medium from growing such cells is tested for the presence of the desired protein. Positive pools are selected and the clones used to make the pool are screened to identify and isolate the clone containing the desired DNA.

8 Claims, 3 Drawing Figures

METHOD FOR IDENTIFICATION AND ISOLATION OF DNA ENCODING A DESIRED PROTEIN

FIELD OF THE INVENTION

This invention relates to the identification and isolation of DNA encoding desired protein, particularly to the identification and isolation of clones containing such DNA by expression screening using only an assay for detecting the desired protein. The assay can be based on immune reactions, enzyme reactions, or other biological activities.

BACKGROUND OF THE INVENTION

Recently developed techniques of molecular cloning make it possible to clone a nucleotide sequence which encodes a protein and to produce that protein in quantity using a suitable host-vector system (Maniatis, T., et al., *Molecular Cloning—A Laboratory Manual* Cold Spring Harbor Laboratory, Cold Spring Harbor, N.Y. 1982). The protein can then be recovered by known separation and purification techniques. Cloning methods which have been used to date can be grouped into three general categories: (1) methods based upon knowledge of the protein structure, for example, its amino acid sequence; (2) methods based upon identification of the protein expressed by the cloned gene using an antibody specific for that protein; and (3) methods based upon identification of an RNA species which can be translated to yield the protein or activity encoded by the gene of interest.

Each of these classes of methods becomes difficult to apply when the protein of interest (and its corresponding mRNA) is produced in very low amount. Thus, if it is difficult to obtain an adequate quantity of purified protein, then it is difficult to determine the amino acid sequence of the protein. Similarly, identification of an expressed protein by antibody binding is preferentially carried out using a high-titer monospecific polyclonal antiserum. Such an antiserum cannot be obtained in the absence of quantities of the pure protein (antigen). A monoclonal antibody offers an alternative approach, but the required antibody can also be difficult to obtain in the absence of suitable antigen, and such monoclonal antibody may not react with the protein in the form in which the protein is expressed by available recombinant host-vector systems. Finally, translation of an RNA species to yield an identifiable protein or activity requires that the RNA in question be present in the RNA source in sufficient abundance to give a reliable protein or activity.

Among the methods listed above, RNA translation has been the most generally applicable procedure for identifying cDNA clones corresponding to rare mRNAs. In a common embodiment of this procedure, cDNA clones carrying sequences complementary to specific mRNAs are identified by hybridization selection. The cloned DNAs are denatured individually or in groups, immobilized on a solid matrix, and hybridized to preparations of mRNA. The RNA-DNA duplex is heated to release the mRNA, which is then translated in cell-free, protein-synthesizing systems or in Xenopus oocytes. The translation products are identified by immunoprecipitation and/or SDS-polyacrylamide gel electrophoresis or by biological assays.

A serious limitation to the use of RNA translation methods is the difficulty of obtaining an adequate signal from the translation product of a rare mRNA. It may be possible to enrich for a desired mRNA by various procedures; two principal methods are size fractionation and removal of RNA sequences which are shared with RNA preparations from cells which do not produce the protein of interest. However, detection of a translation product ultimately depends upon the sensitivity of the assay for the protein of interest. In the case where an RNA is rare and the assay for its translation product is relatively insensitive, the amount of protein produced by oocyte translation may be below the threshold of detection in the assay.

A more direct approach to isolation of specific cDNA clones could be based upon identification of protein products of cDNA clones in an expression vector. An expression vector is a self-replicating DNA element which contains signals for efficient transcription and translation of a cDNA which is inserted into it. In the past, expression vectors have mainly been used for manufacturing quantities of protein after isolation of a clone by traditional means. As noted above, RNA translation methods produce proteins according to the abundance of specific mRNAs, so that a rare mRNA may generate an undetectable quantity of protein. Expression vectors, by contrast, express the protein product of each cDNA insert at an equally high level. Thus the product of a rare mRNA will in general be more easily detected using an expression vector rather than RNA translation.

Cloning by expression has been carried out previously in a general sense in bacteria and in yeast. For example, complementation of a bacterial or a yeast mutation by transformation with an appropriate clone library has been used to isolate a number of microbial genes. Attempts at antibody identification of mammalian protein expressed in a bacterial host-vector system, as described above, constitute another example of this approach. However, mammalian proteins which are of commercial interest, particularly as therapeutic agents, are often secreted proteins containing carbohydrates and/or numerous disulphide bonds. Because of these attributes, it is often the case that a mammalian protein synthesized in a microbial host-vector system is expressed in an inactive form and/or with altered antigenic determinants and thus cannot be identified by activity or antibody assays.

The use of a mammalian host-vector system for expression cloning of mammalian cDNAs has been attempted in the past (Okayama, H. and Berg, P. 1983 Mol. Cell Biol. 3 280–289). Mammalian host-vector systems employing transient expression of genes in COS-1 cells have often been used to verify the identity of cDNA clones isolated by standard techniques (e.g. Gray et al 1982 Nature 295 503–508; Yokota et al 1984 Proc. Nat. Acad. Sci. 81 1070–1074). However, there is no report in the literature of a cDNA clone identified directly by the activity of its protein produced in a mammalian expression system.

Thus, it can be seen that it would be desirable to have a method for isolation of specific cDNA clones by assay of proteins produced in a mammalian expression system, particularly for cloning cDNAs corresponding to rare mRNAs.

SUMMARY OF THE INVENTION

The present invention provides a new method for identifying and isolating clones containing DNA coding for a desired protein. DNA prepared from a cell that expresses the desired protein is inserted into an isolation expression vector having means for replication (as a means of producing DNA) and a suitable promoter for expression of said DNA in a predetermined mammalian host cell as well as means for replication in a bacterial cell. The transient expression vector is then inserted into a bacterial cell for replication of the DNA. Pools of DNA, prepared from a predetermined number of bacterial clones so that the nucleic acids (DNA and RNA) are substantially free of other bacterial contaminants are transfected or microinjected into mammalian host cells and conditioned medium from growing such cells is tested for the presence of the desired protein. Positive pools are selected and the clones used to make the pool are screened to identify and isolate the clone containing the desired DNA.

In one embodiment of the present invention a method for identifying and isolating clones containing cDNA coding for a desired protein comprising:

preparing RNA from a cell that produces said protein;

preparing polyadenylated messenger RNA from said RNA;

preparing single stranded cDNA from said messenger RNA;

converting the single stranded cDNA to double stranded cDNA;

inserting the double stranded cDNA into isolation expression vectors and transforming bacteria with said vector to form colonies;

picking pools of a predetermined number of said colonies and separating said isolation expression vectors from each pool;

transfecting or microinjecting said isolation expression vectors from each pool into suitable host cells for expressing said protein;

culturing the host cells and assaying the culture medium for presence of said protein; and selecting positive pools and screening the colonies used to make the pool to identify a colony or colonies responsible for expressing said protein.

DETAILED DESCRIPTION OF THE INVENTION

The following definitions are supplied in order to facilitate the understanding of this case. To the extent that the definitions vary from meaning circulating within the art, the definitions below are to control.

Downstream means the direction going towards the 3' end of a nucleotide sequence.

An enhancer is a nucleotide sequence that can potentiate the transcription of a gene independent of the position of the enhancer in relation to the gene or the orientation of the sequence.

A gene is a deoxyribonucleotide sequence coding for a given protein. For the purposes herein, a gene shall not include untranslated flanking regions such as RNA transcription initiation signals, polyadenylation addition sites, promoters or enhancers.

Isolation expression vector as used herein means the vector used for transfection or microinjection of cDNA into a host for expression of the desired protein to identify and isolate the desired gene. This vector may or may not be suitable for expression in quantity, e.g. by transformation of eukaryotic or prokaryotic cells.

Ligation is the process of forming a phosphodiester bond between the 5' and 3' ends of two DNA strands. This may be accomplished by several well known enzymatic techniques, including blunt end ligation by T4 ligase.

Orientation refers to the order of nucleotides in a DNA sequence. An inverted orientation of a DNA sequence is one in which the 5' to 3' order of the sequence in relation to another sequence is reversed when compared to a point of reference in the DNA from which the sequence was obtained. Such points of reference can include the direction of transcription of other specified DNA sequences in the source DNA or the origin of replication of replicable vectors containing the sequence.

Replication means the process by which cells make copies of DNA.

Transcription means the synthesis of RNA from a DNA template.

Transformation means changing a cell's genotype by the cellular uptake of exogenous DNA. Transformation may be detected in some cases by an alteration in cell phenotype. Transformed cells are called transformants. Pre-transformation cells are referred to as parental cells.

Transient expression systems as used herein means the host-vector system used for identification and isolation of a desired gene. This system may or may not be suitable for expression in quantity.

Translation means the synthesis of a polypeptide from messenger RNA.

In order to identify and isolate a clone containing DNA coding for a desired protein or factor in accord with one embodiment of the present invention, a novel procedure is described that requires only an assay technique for detecting the expression of the gene. This procedure uses a host-vector system that expresses very high levels of protein from inserted cDNAs.

First, a cell that produces the desired protein or factor is identified. The mRNA of the cell is then harvested. If the desired mRNA is membrane bound such as, for example, the mRNA of secreted proteins such as lymphokines, the membrane bound mRNA is separated from free mRN in the cells. This separation is believed to enrich the collected mRNA 5–10 times for membrane bound sequences and thus reduces the effort involved in identifying the desired clone. Other techniques can be used to fractionate the mRNA, e.g. urea agarose, gel electrophoresis, etc. However, such separation is not required for the process of the present invention. Polyadenylated messenger RNA is then prepared by chromatography on oligo dT cellulose.

A cDNA library is prepared from the mRNA such that the cDNAs are inserted directly into an isolation expression vector suitable for transfection into a host capable of expressing the desired protein. To construct this library, first strand cDNA is prepared by standard methods using the mRNA prepared above. The RNA/cDNA hybrid is then converted to double-stranded cDNA form and then inserted into the transient expression vector. It is preferred to insert the cDNAs using linkers rather than by tailing because tailing may hinder expression which could affect detection of rare proteins or factors.

A preferred host-vector system for the isolation of a clone containing DNA coding for a mammalian protein or factor is based on transient expression of the cDNA by a suitable vector in mammalian cells. In accord with the present invention, a preferred expression system is based on the CV-1 monkey cell lines transformed with a replication-origin-defective SV40 DNA molecule (Gluzman, Y., Cell 23 175–182, 1981). The transformed monkey CV-1 cells, designated COS (CV-1, origin defective, SV40), do not produce SV40 virus, but produce high levels of large T antigen and are permissive for SV40 DNA replication. They also efficiently support the replication of SV40 virus containing deletions in the early region and of bacterial plasmids with an SV40 replication origin (Myers, R. M. & Tjian, R. 1980 PNAS 77 6491–6495). Thus, this system provides a means of amplifying transfected exogenous DNA via SV40 mediated DNA replication in order to increase the level of mRNA and protein expressed from the exogenous DNA. It is possible to transiently introduce exogenous genes into a subpopulation of cells such that the subpopulation will express the desired product over a period of several days (Mellon, P., V. Parker, Y. Gluzman, T. Maniatis 1981 Cell 27 279–288). Other similar systems are also useful in the practice of this invention.

When a cDNA library in an appropriate vector is transfected into cells such as COS cells, the desired product will only be expressed by the subpopulation of cells which has incorporated the cDNA clone encoding that product. In order that this subpopulation of cells will express a sufficient quantity of the desired product to be detectable in the appropriate assay, it is essential that the host-vector system express proteins abundantly. Abundant expression is preferably achieved by incorporating into the vector components that increase production and/or stability of DNA, RNA, or protein or a combination of these compounds. As noted above, in accord with a preferred embodiment of the invention, the use of COS cells together with a vector containing an SV40 replication origin causes amplification of the transfected DNA. Vectors used for transient expression in mammalian cell systems will also preferably contain elements such as promoters, enhancers, introns, polyadenylation sites, 3' noncoding regions, and translational activators, as will be discussed below.

The isolation expression vectors useful herein may include enhancers. Preferred enhancers for use with mammalian cells are obtained from animal viruses such as simian virus 40, polyoma virus, bovine papilloma virus, retrovirus or adenovirus. Ideally, the enhancer should be from a virus for which the host cell is permissive, i.e. which normally infects cells of the host type. Viral enhancers may be obtained readily from publicly available viruses. The enhancer regions for several viruses, e.g., Rous sarcoma virus and simian virus 40, are well known. See Luciw et al., Cell 33:705–716 (1983). It would be a matter of routine molecular biology to excise these regions on the basis of published restriction maps for the virus in question and, if necessary, modify the sites to enable splicing the enhancer into the vector as desired. For example, see Kaufman et al, J. Mol. Biol., 159:601–621 (1982) and Mol. Cell Biol. 2(11):1304–1319 (1982). Alternatively, the enhancer may be synthesized from sequence data; the sizes of viral enhancers (generally less than about 150 bp) are sufficiently small that this could be accomplished practically.

A polyadenylation splicing (or addition) site is a DNA sequence located downstream from the translated regions of a gene, and adenine ribonucleotides are added to form a polyadenine nucleotide tail at the 3' end of the messenger RNA. Polyadenylation is important in stabilizing the messenger RNA against degradation in the cell, an event that reduces the level of messenger RNA and hence the level of product protein.

Eucaryotic polyadenylation sites are well known. A concensus sequence exists among eucaryotic genes: the hexanucleotide 5'-AAUAAA-3' is found 11–30 nucleotides from the point at which polyadenylation starts. DNA sequences containing polyadenylation sites may be obtained from viruses in accord with published reports. Exemplary polyadenylation sequences can be obtained from mouse beta-globin, and simian virus 40 late or early region genes, but viral polyadenylation sites are preferred. Since these sequences are known, they may be synthesized in vitro and ligated to the vectors in conventional fashion.

A polyadenylation region must be located downstream from the gene coding for the desired protein. The sequence which separates the polyadenylation site from the translational stop codon is preferably an untranslated DNA oligonucleotide such as an unpromoted eucaryotic gene. The oligonucleotide should extend for a considerable distance, on the order of up to about 1,000 bases, from the stop codon to the polyadenylation site. This 3' untranslated oligonucleotide generally results in an increase in product yields.

The presence of introns in the untranslated transcribed portion of the vector may increase expression. Such introns may be obtained from other sources than either the host cells or the gene source. They may also be hybrids prepared from two sources. For example, an intron comprising a 5' splice site from the second intron of the adenovirus tripartite leader and a 3' splice site from a mouse immunoglobulin gene can be used effectively to increase the efficiency of mRNA production and export to the cellular cytoplasm. Insertion of this hybrid intron downstream from the adenovirus major late promoter and cDNA copy of the tripartite leader but preceding the gene sequence to be expressed can lead to increased yield of the desired gene product.

In a preferred embodiment of the present invention, the cloning and isolation expression vector contains a translational activator gene. Translational activators are genes which encode either protein or RNA products which affect translation of a desired mRNA. The best known example is the adenovirus virus-associated (VA) gene (VA I) which is transcribed into a short RNA species that interacts with sequences in the 5' untranslated region of the adenovirus major late mRNAs (Thimmappaya et al., 1982 Cell 31 543). The necessary sequences for translational activation by VA RNA lie within the adenovirus late mRNA tripartite leader. The adenovirus tripartite leader is spliced together from noncontiguous regions of the adenovirus genome and is present on the 5' end of the adenovirus major late transcripts. VA I RNA can activate translation of mRNAs which contain the tripartite leader sequence. Thus, the preferred cDNA cloning and expression vector contains the adenovirus VA genes and the tripartite leader preceding the cDNA, such that a hybrid mRNA will be transcribed with the tripartite leader sequences at the 5' end. Other translational activators can also be used in accord with the present invention.

These vectors can be synthesized by techniques well known to those skilled in this art. The components of the vectors such as enhancers, promoters, and the like may be obtained from natural sources or synthesized as described above Basically, if the components are found in DNA available in large quantity (e.g. components such as viral functions) then with appropriate use of restriction enzymes large quantities of the component may be obtained by simply culturing the source organism, digesting its DNA with an appropriate endonuclease, separating the DNA fragments, identifying the DNA containing the element of interest and recovering same. Ordinarily, a transformation vector will be assembled in small quantity and then ligated to a suitable autonomously replicating synthesis vector such as a procaryotic plasmid or phage. The pBR322 plasmid, or a variation thereof, can be used in most cases. See Kaufman et al., op. cit.

Synthesis vectors are used to clone the ligated transformation vectors in conventional fashion, e.g. by transfection of a permissive procaryotic organism, replication of the synthesis vector to high copy number and recovery of the synthesis vector by cell lysis and separation of the synthesis vector from cell debris.

In one embodiment of the invention, isolation expression vectors containing cDNA prepared from a cell that produces a desired protein or factor are transfected into E. coli and plated out on petri dishes at approximately 2000 colonies per dish. The isolation expression vectors are preferably high copy number vectors or capable of amplification in the bacterial cells by chloramphenicol. High copy number vectors are vectors that replicate at least about 10 times greater than pBR322. The colonies are lifted off onto a nitrocellulose filter, designated as the master filter. Replica filters, and hence replicas of the colonies, are·made and aligned with the original so that sections of the replica filters can be identified with the corresponding portion of the master filter. Although the DNA could be isolated from each colony individually for transient expression, it is generally not practical to do so because it is generally necessary to screen large numbers of clones. Thus, in accord with the present invention, it is preferred that the cDNA clones be treated as units within heterogeneous pools of cDNAs for transient expression. The DNA (expression vector with cDNA insert) is generally prepared from a pool of colonies from the replica filters and transfected or microinjected into host cells for expression of the protein or factor, and detection of such expression. We have found that care must be used to prepare the DNA for transfection. It is important to eliminate all contaminants of bacterial origin from the nucleic acids (RNA and DNA). However, the DNA need not be isolated from the RNA.

DNAs are prepared from pools containing a predetermined number of colonies, corresponding to the colonies on one or more replica filters or on a section of a replica filter. The number of colonies per pool is determined by the yield of protein or factor from the transient expression system as discussed above, and by the sensitivity of the detection system or assay for the expressed product.

The consideration of these factors will be illustrated for the isolation expression vector and system described in the examples. More explicitly, using p91023(B) with a correctly inserted secreted protein gene such as, for example, gamma interferon or interleukin 2, and $10^6$ COS cells, 0.1 to 1.0 ug/ml of the secreted protein can routinely be found in the COS cell medium. This amount of protein corresponds to approximately 10,000-100.000 units/ml of gamma interferon activity. Because gamma interferon can be reliably detected at a concentration of 1 unit/ml, these results suggest that DNA of vector p91023(B) containing a cDNA insert encoding, for example, gamma interferon could be diluted 10,000-fold with other DNA prior to transfection, and would still yield detectable gamma interferon activity in the COS cell medium.

Some variability is introduced into the procedure by the fact that DNAs used for screening cDNA libraries are prepared from pools of colonies in which some colonies may be smaller than others. This variability in size of colonies, together with some allowance for day-to-day variations in the behavior of the COS cells, suggests that a ten-fold reduction factor should be incorporated into estimates of the efficiency of detection. Inclusion of such a factor suggests that gamma interferon activity should be *routinely* detectable in the medium from COS cells transfected with DNA prepared from a pool of 1000 colonies among which is present one colony containing a gamma interferon cDNA in vector p91023(B).

For a system as described above, for pools of 500-1000 heterogeneous colonies with each colony at about 3 mm in diameter and each containing an expression vector with a cDNA insert, gamma interferon, interleukin-2 (IL2) and colony stimulating factor (CSF) were definitively detected due to the expression of the DNA from a single colony where the insert cDNA was the gene for gamma interferon, interleukin 2 or colony stimulating factor, respectively. In other words, in accord with the present invention, the presence of a single colony with an expression vector containing a particular expressable cDNA insert coding for one of the above proteins within a pool of 500-1000 colonies (each colony carrying an expression vector having a different cDNA insert), can be detected by assaying for the expression product of that particular cDNA insert among the expression products of the pool of 500-1000 vectors containing heterogeneous cDNA inserts.

This method can be applied to other expression systems in a similar manner by determining for the transient expression system, the expression levels and capabilities of the system in which the desired protein or factor is expressed and by determining the sensitivity of the detection system.

Once an estimate for the maximum permissible pool size has been determined, the colonies from each filter or section are scraped into medium such as L-Broth, the bacteria are collected by centrifugation and the plasmid DNA expression vectors containing the cDNA inserts are isolated and transfected into a suitable host for expression of protein, e.g. a mammalian cell for mammalian proteins. The preferred synthesis vector herein is a mutant of the E. coli plasmid pBR322 in which sequences have been deleted that are deleterious to replication in eucaryotic cells. See Kaufman et al., op. cit. Use of this mutant obviates any need to delete the plasmid residue prior to transfection. For a secreted protein, the medium from the transfected cells is recovered and assayed for the desired protein or effect. For non-secreted proteins or factors, the COS cells themselves are harvested. A positive assay indicates that a colony containing cDNA coding for the desired protein or factor is on a particular filter or section of a filter.

To determine which of the clones on the section of the original master filter contains the desired cDNA, each clone on the filter section is picked and grown. The cultures are then placed in a matrix. Pools are prepared from each horizontal row and vertical column of the matrix. DNA samples are prepared from each pool and transfected into the host cells for expression. Samples from these transfected cells are assayed for the expression of the desired protein or factor. One vertical column pool and horizontal row pool should produce a positive assay. The clone common to these pools will contain the desired cDNA. If the matrix contains more than one positive clone, more than one column and row will be positive. In such case, further screening of a small number of clones may be necessary.

The desired cDNA is excised from the clones by restriction enzymes and can be sequenced by known techniques. It can be readily appreciated that the procedure described herein can be used to obtain cDNA clones from any source as long as the expression product can be detected.

Any protein or factor that can be detected by an assay can be cloned by the process of the present invention. Thus, the process requires obtaining essentially full length cDNA, i.e. cDNA that codes for a detectable protein or factor. For immunological detection systems, the product of a less than full length cDNA can present an antigenic determinant. The smaller the size of the protein or factor, the more likely that its complete coding region will be obtained. Thus, the method of this invention favors relatively small proteins or factors. With careful preparation molecules encoded by cDNA having up to about 4000 nucleotides can be cloned by the process of the present invention. Preferably, the process of the invention is used to clone proteins encoded by cDNA having up to about 2000 nucleotides, and more preferably up to about 1200 nucleotides. Thus, proteins having a molecular weight up to at least about 100,000 daltons, preferably about 50,000 daltons or less, can be cloned by the process of the present invention.

Once the desired protein gene is cloned, the gene can be expressed in quantities by transforming a vector containing the gene into a stable cell line in accord with well known techniques. Host-vector systems for the expression of the desired protein or factor may be procaryotic or eucaryotic, including yeast, mammalian and insect. Expression is accomplished by transforming procaryotic or eucaryotic cells with a suitable vector containing the gene for the desired protein. The DNA sequence obtained from a mammalian source by the above described procedure can be expressed directly in mammalian cells under the control of a suitable promoter.

Typically, promoters that are heterologous to the desired gene are used to obtain high level expression by techniques that are well-known by those skilled in the art. In order to express the protein in procaryotic systems, the N-terminus of the mature protein must be determined. This can be done using standard techniques known by those skilled in the art. Thus, once the desired gene is isolated and identified, means well-known by those skilled in the art are utilized to express the gene product in quantities. Typically, such expression will be accomplished using a different host-vector system than was used to identify and isolate the gene. A protein thus produced (e.g. by procarytic systems) may have a methionine group at the N-terminus of the protein (herein called Met-protein). The mature proteins produced by procaryotic and eucaryotic cells will be otherwise identical in amino acid sequence, but the eucaryotic product may be glycosylated.

The protein expressed in appropriate procaryotic or eucaryotic cells can then be recovered by purification and separation techniques well known to those skilled in the art.

The invention will be further understood with reference to the following illustrative embodiments, which are purely exemplary, and should not be taken as limitive of the true scope of the present invention, as described in the claims.

In the examples, unless otherwise specified, temperatures are in °C. Also, restriction endonucleases are utilized under the conditions and in the manner recommended by their commercial suppliers. Ligation reactions are carried out as described by Maniatis et al., supra at 245–6, the disclosure of which is incorporated herein by reference, using the buffer described at page 246 thereof and using a DNA concentration of 1–100 ug ml, at a temperature of 23° C. for blunt ended DNA and 16° C. for "sticky ended" DNA. Electrophoresis is done in 0.5–1.5% agarose gels containing 90 mM Tris-acetate (pH 8), 1 mM EDTA. All radiolabelled DNA is labelled with $^{32}P$, whatever labelling technique was used.

EXAMPLE A—Isolation and Identification of CSF cDNA

Step 1. Mo Cell Line Cultures

Mo cells (ATCC CRL 8066) were grown routinely in Alpha (6% $CO_2$) or Iscove's (10% $CO_2$) medium containing 20% Fetal Calf Serum (FCS), 2mM glutamine, 100 U/ml streptomycin and 100 ug/ml penicillin. The cells should be subcultured every 4–5 days. Cells are counted and seeded into Falcon T-175 flasks in 100–150 ml medium at density of $3-4 \times 10^5$ cells/ml. Cells will double in 20% FCS every 4–7 days. Growth rate is not constant and cells may sometimes appear to stop growing then go through bursts of growth. Mo cells can be grown in serum-free medium. Survival is much better when cells are not washed when transferred from FCS to serum-free medium. Optimal density in Serum-Free medium (SF) is $5 \times 10^5$ cells/ml. Cells will grow slightly (or at least maintain constant number) for 3 days in serum-free medium, and then should be fed 20% FCS for at least 4 days. This growth schedule (3 days SF, 4 days 20% FCS) can be repeated weekly if SF medium is required, with no apparent harm to the cells for several months.

Step. 2 Assays for CSF Activity

A. Bone Marrow Assay

.Obtain fresh bone marrow. Break apart spicules by drawing through 20, 22, then 25 gauge needle. Dilute 1:1 with sterile phosphate-buffered saline (PBS) (room temperature) and layer over Ficoll-Paque (about 30 ml BM-PBS over 6 ml Ficoll). Spin at 1500 rpm for 40 minutes at room temperature. Remove fat and PBS layer and discard. Pipette off the light density layer. Wash 2× with PBS and count. Plate cells in RPMI (purchased from GIBCO as RPMI 1640) plus 10% HIFCS (heat inactivated FCS) and incubate at 37° C. for 3 hours to remove adherent cells.

Plating medium (make fresh):
20% FCS
0.3% agar dissolved in $H_2O$ cooled to 40° C.

2× Iscoves (1:1 v/v with Agar)
final concentration of 100 U/ml penicillin and 100 ug/ml streptomycin
$10^{-4}$M alpha thioglycerol in 2× Iscoves medium from $10^{-2}$ M stock Cool agar to about 40°. Mix with other ingredients. Cool in $H_2O$ bath to 37°–38° and hold at that temperature.

After 3 hours, pipette off the non-adherent cells. Spin and count. Add $2 \times 10^5$ cells/ml of plating medium and keep in controlled temperature water bath at 37°–38°. Add samples (e.g., medium from transfected cells; usually 10 ul sample) to the first row of wells of a microtiter plate in duplicate. Add 100 ul cell suspension to each well. Add additional 50 ul of cell suspension to each well in the first row. Mix thoroughly and transfer 50 ul of solution from the first row into the next row, etc. and continue 1:3 dilutions across plate. Wrap the plate in parafilm. Incubate 10–14 days at 10% $CO_2$, 37° C. in fully humidified atmosphere and score colonies.

To score the colonies, the total number of colonies that grow in each well is counted. In each assay, several wells are plated without including a sample (blank) to obtain a background colony count. The average number of colonies that grow in the blank wells is subtracted from the number of colonies found in each of the wells containing samples. One unit of CSF is the amount that will stimulate the formation of one colony above the background level per $10^5$ human bone marrow cells (plated at $10^5$ cells per ml) when the CSF concentration is sub-saturating. The CSF activity is determined by dilution and comparing the number of colonies at various dilutions to find the concentration just below the saturation level.

For this assay, the colonies containing granulocytes, monocytes or both types of cells are counted. The types of cells in the colonies are determined by picking colonies and staining individual cells.

B. KG-1 Cell Assay

KG-1 cells (*Blood,* Vol. 56, No. 3 (1980)) are grown in Iscoves medium + 10% FCS passed twice per week and seeded for each passage at $2 \times 10^5$ cells/ml. The cells are used for assay only between passage 30–35. The assay is the same as for bone marrow as described above, except the KG-1 cells are plated in agar mixture at $4 \times 10^3$ cells/ml.

The number of colonies growing in each well is determined and the background count is subtracted as in the Bone Marrow assay described above. One KG-1 CSF unit/ml is that concentration of CSF that will stimulate half of the maximum number (saturation) of KG-1 colonies to grow. The maximum number is obtained by including a saturating level of CSF in several wells.

Step 3. Construction of Isolation Expression Vector p91023(B)

Figure 1:
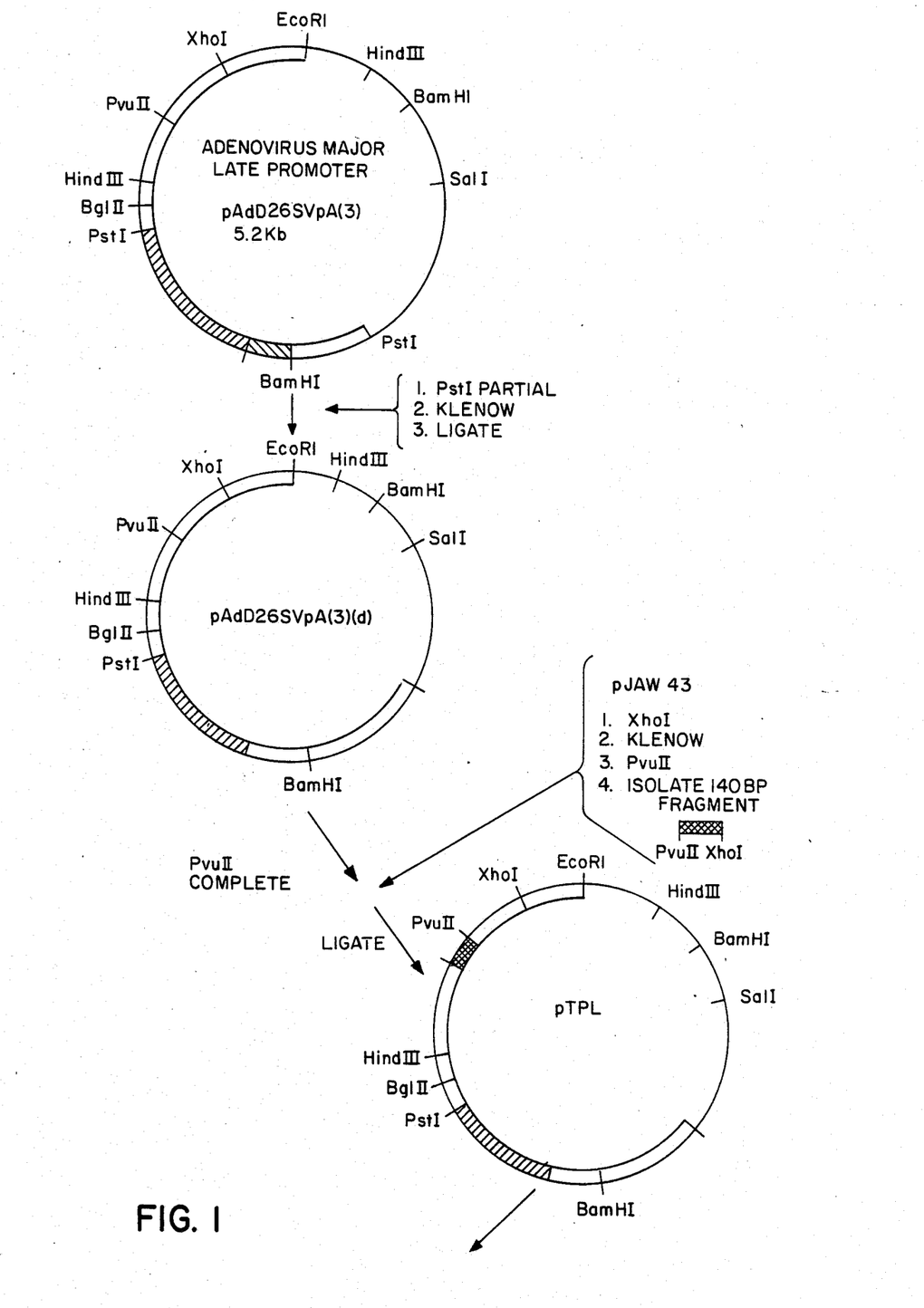
FIG. 1 is a schematic illustrating the preparation of plasmid pTPL from plasmid pAdD26SVpA(3).

The transformation vector pAdD26SVpA(3) was described by (Kaufman et al., Mol. Cell Biol. 2(11):1304–1319 [1982]. It has the structure illustrated in FIG. 1. Briefly this plasmid contains a mouse dihydrofolate reductase (DHFR) cDNA gene that is under transcriptional control of the adenovirus 2 (Ad2) major late promoter A 5' splice site from the second intron of the tripartite leader and a 3' splice site derived from an immunoglobulin gene are present between the Ad2 major late promoter and the DHFR coding sequence. The SV40 early polyadenylation site is present downstream from the DHFR coding sequence. The procaryotic-derived section of pAdD26SVpA(3) is from pSVOd (Mellon, P., Parker, V., Gluzman, Y. and Maniatis, T. 1981, Cell 27:279–288) and does not contain the pBR322 sequences known to inhibit replication in mammalian cells (Lusky, M., and Botchan, M. 1981, Nature (London) 293:79–81).

pAdD26SVpA(3) was converted into plasmid pCVSVL2 as illustrated in FIG. 1. pAdD26SVpA(3) was converted into plasmid pAdD26SVpA(3)(d) by deletion of one of the two PstI sites in pAdD26SVpA(3). This was accomplished by a partial digestion with PstI (using a deficiency of enzyme activity so that a subpopulation of linearized plasmids can be obtained in which only one PstI site is cleaved), then treatment with Klenow fragment of Pol I to blunt the ends, ligation to recircularize the plasmid, transformation of *E. coli* and screening for deletion of the PstI site located 3' of the SV40 polyadenylation sequence.

The adenovirus tripartite leader and virus associated genes (VA genes) were inserted into pAdD26SVpA(3)(d) as illustrated in FIG. 1. First, pAdD26SVpA(3)(d) was cleaved with PvuII to make a linear molecule opened within the 3' portion of the first of the three elements comprising the tripartite leader. Then, pJAW 43 (Zain et al. 1979, Cell 16 851) was digested with Xho 1, treated with Klenow, digested with PvuII, and the 140 base pair fragment containing the second leader and part of the third leader was isolated by electrophoresis on an acrylamide gel (6% in Tris borate buffer; Maniatis et al. [1982] supra). The 140 bp fragment was then ligated to the PvuII digested pAdD26SVpA(3)(d). The ligation product was used to transform *E. coli* to tetracycline resistance and colonies were screened using the Grunstein-Hogness procedure using a $^{32}P$ labelled probe hybridizing to the 140 base pair fragment. DNA was prepared from positively hybridizing colonies to test whether the PvuII site reconstructed was 5' or 3' of the inserted 140 base pair DNA specific to the 2nd and 3rd adenovirus late leaders. In the correct orientation, the PvuII site is on the 5' side of the 140 base pair insert. This plasmid is designated pTPL in FIG. 1.

Figure 2:
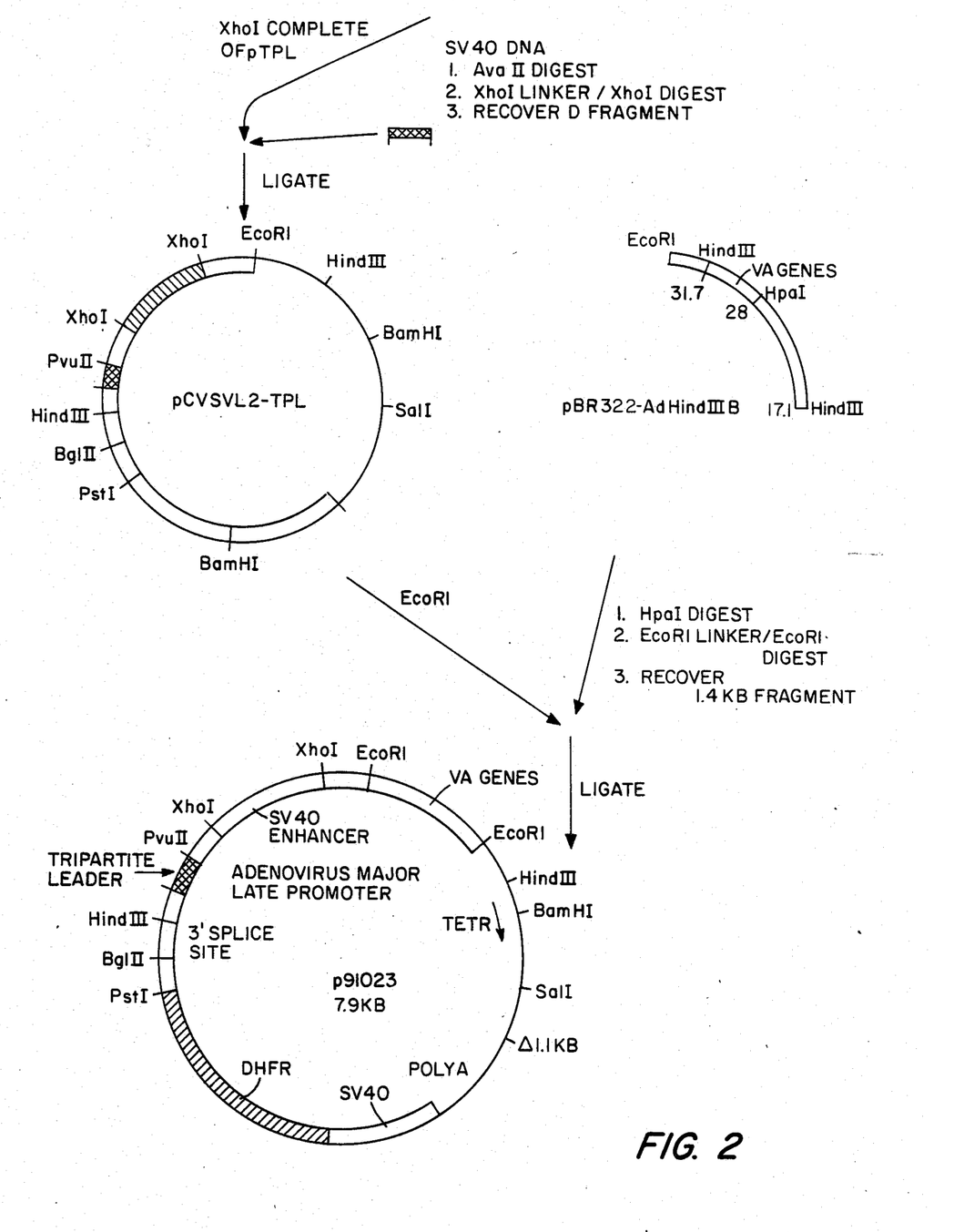
FIG. 2 is a schematic continuing from FIG. 1 and illustrating the preparation of plasmid p91023 from plasmid pTPL.

The Ava II D fragment of SV40 containing the SV40 enhancer sequence was obtained by digesting SV40 DNA with Ava II, blunting the ends with Klenow fragment of Pol I, ligating Xho 1 linkers to the fragments, digesting with Xho 1 to open the Xho 1 site, and isolating the fourth largest (D) fragment by gel electrophoresis. This fragment was then ligated to Xho I cut pTPL yielding the plasmid pCVSVL2-TPL (FIG. 2). The orientation of the SV40 D Fragment in pCVSVL2-TPL was such that the SV40 late promoter was in the same orientation as the adenovirus major late promoter.

To introduce the adenovirus virus associated (VA) genes into the pCVSVL2-TPL, first a plasmid was constructed that contained the adenovirus type 2 Hind III B fragment. Adenovirus type 2 DNA was digested with Hind III and the B fragment was isolated after gel electrophoresis. This fragment was then inserted into pBR322 which had previously been digested with Hind III. After transformation of *E. coli* to ampicillin resistance, the recombinants were screened for insertion of the Hind III B fragment and the inserted orientation was determined by restriction enzyme digestion. pBR322 - Ad Hind III B contains the adenovirus type 2 Hind III B fragment in the orientation depicted in FIG. 2.

As illustrated in FIG. 2, the VA genes were conveniently obtained from plasmid pBR322-Ad Hind II by digesting with Hpa I, ligating EcoRl linkers and digesting with EcoRl, and recovering the 1.4kb fragment. This fragment having EcoRl sticky ends was then ligated into the EcoRl site of pCVSVL2-TPL (which had previously been digested with EcoRl). After transformation of *E. coli* HB101 and selection for tetracycline resistance, colonies were screened by filter hybridization to a DNA probe specific to the VA genes. DNA was prepared from positively hybridizing clones and characterized by restriction endonuclease digestion. The product plasmid was designated p91023.

The 2 EcoRl sites in p91023 were removed. p91023 was cut to completion with EcoRl, generating two DNA fragments: one, about 7Kb and, the other, a 1.4 Kb fragment containing the VA genes. The ends of both fragments are filled in using the Klenow fragment of PolI, and then both fragments, i.e. 1.3 Kb and 7Kb, were religated together. A plasmid p91023(A) containing the VA genes and similar to p91023 but deleted for the 2 EcoRl sites was identified by Grunstein-Hogness screening with the VA gene fragment, and by conventional restriction site analysis.

Figure 3:
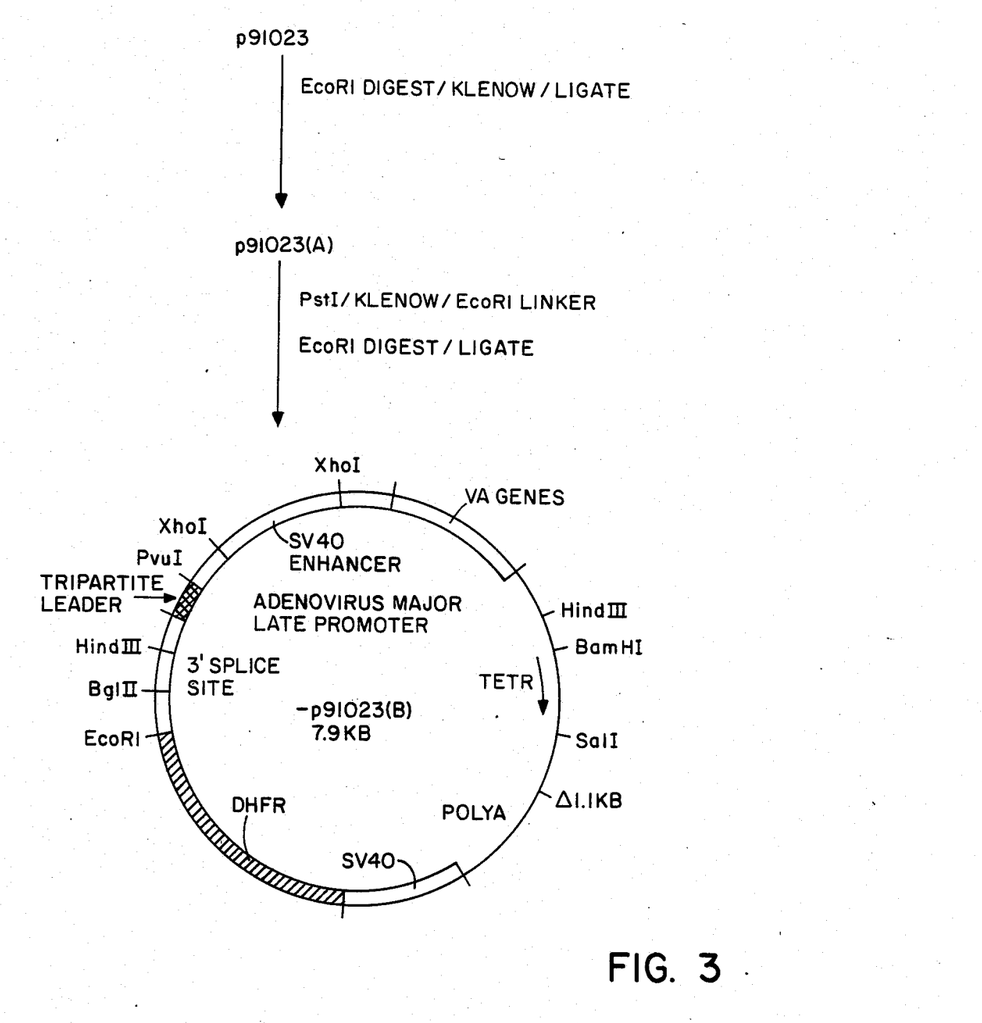
FIG. 3 is a schematic continuing from FIG. 2 and illustrating plasmid p91023(B).

Then the single PstI site in p91023(A) was removed and replaced with an EcoRl site (FIG. 3). p91023(A) was cut to completion with PstI, and then treated with Klenow fragment of PolI to generate flush ends. EcoRl linkers were ligated to the blunted PstI site of p91023(A). The linear p91023(A), with EcoRl linkers attached at the blunted PstI site, was separated from unligated linkers and digested to completion with EcoRl, and then religated. A plasmid p91023(B) was recovered and identified to have a structure similar to p91023(A), but with an EcoRl site situated at the previous PstI site.

Step 4. Preparation of cDNA Library

Mo cells were induced for 16–20 hrs. with phytohaemagglutinin (PHA) and 12,O-tetradecanoylphorbol-13-acetate (TPA) to enhance their lymphokine production. Cells were plated at $5 \times 10^5$ cells/ml in Iscove's medium with 20% FCS, 0.3% (v/v) PHA and 5 ng/ml TPA. The cells were collected by centrifugation. The pelleted cells were resuspended in 20 ml of ice cold hypotonic lysis buffer (RSB buffer: 0.01M Tris-HCl, PH 7.4, 0.01M KCl, 0.0015M MgCl$_2$, 1 ug/ml cycloheximide, 50 units/ml RNAsin and 5mM dithiothreitol). The cells were allowed to swell on ice for five minutes then were ruptured mechanically with 10 strokes of a tight fitting dounce glass homogenizer. The homogenate was centrifuged at low speed (2000 RPM in a Beckman J6 centrifuge) to remove nuclei and unlysed cells. The supernatant was held on ice while the nuclear pellet was resuspended in 10 ml of RSB and re-centrifuged at low speed. This second supernatant was pooled with the first and the combined supernatants were centrifuged at low speed to remove residual contamination with nuclei and unlysed cells. The supernatant from this spin was brought to 0.15M KCl by addition of 2M KCl then centrifuged at high speed (25,000 RPM, Beckman SW 28 rotor for 30 minutes) to pellet the membranes. The membrane pellet was carefully washed with cold RSB then resuspended in 12 ml of RSB containing 2 M sucrose and 0.15M KCl. Two discontinuous gradients were prepared in Beckman SW41 centrifuge tubes by layering 6 ml of the membrane solution in 2 M sucrose over 2 ml of RSB with 2.5 M sucrose and 0.15M KCl. The tubes were filled to the top by overlaying with 2.5 ml of RSB containing 1.3M sucrose and 0.15M KCl. These gradients were spun for 4 hours at 27,000 RPM (Beckman, SW41 rotor) at 4° C. The membrane layer (at the interface between the 2.0M and 1.3M sucrose) was carefully removed from the side using an 18 gauge needle and syringe. The membrane fractions from the two gradients were pooled and diluted with 1 volume of distilled H$_2$O then brought to 0.5% Triton X-100 and 0.5% sodium deoxycholate then extracted with an equal volume of phenol. The aqueous layer was re-extracted with a 1:1 mixture of phenol and chloroform and finally an equal volume of chloroform. Finally, the membrane bound RNA was precipitated by addition of NaCl to 0.25M and 2.5 volumes of cold ethanol and incubated overnight at −20° C. The precipitated RNA was collected by centrifugation (4000 RPM for 10 min. in the Beckman J-6 centrifuge) and was resuspended in 1 ml of distilled water. From $2 \times 10^9$ cells, approximately 1 mg of RNA was obtained. The messenger RNA (mRNA) was isolated from the total RNA by chromotography on a 0.5 ml oligo dT-cellulose column. Briefly the RNA was heated to 70° C. for 5 min., quick chilled on ice, then diluted 5 fold with room temperature binding buffer (0.5M LiCl, 0.01M Tris-HCl, pH 7.4, 0.002 M EDTA, and 0.1% SDS). The RNA in binding buffer was passed over the oligo dT-cellulose column equilibrated with binding buffer at room temperature. The column was washed with 5 ml of binding buffer then with 5 ml of 0.15M LiCl, 0.01M Tris-HCl pH7.4, 0.002M EDTA, and 0.1% SDS. Finally, mRNA was eluted with 2 ml of 0.01M Tris-HCl pH7.4, 0.002M EDTA, and 0.1% SDS. The mRNA was precipitated by addition of NaCl to 0.25 M and 2.5 volumes of ethanol and incubation overnight at −20° C. The precipitated mRNA was collected by centrifugation (30,000 RPM for 30 minutes in a Beckman SW55 rotor). The tube was carefully drained and the mRNA pellet was resuspended in 50 ul of H$_2$O. The resuspended mRNA was brought to 0.25M NaCl then extracted 1 time with a 1:1 mix of phenol and chloroform then 3 times with chloroform. The mRNA was precipitated by the addition of 2.5 volumes of ethanol. The mixture was frozen and thawed several times in a dry ice/ethanol bath then centrifuged 15 min. in an Eppendorf centrifuge. The tube was carefully drained and the mRNA pellet was resuspended in 20 ul of distilled H$_2$O. The final yield was approximately 30 ug of mRNA.

First strand cDNA was prepared using standard methods. Briefly, 10 ug of membrane mRNA was diluted into a 100 ul cDNA synthesis reaction mixture containing 300 mM Tris pH 8.4, 140 mM KCl, 10 mM MgCl$_2$, 10 mM B-mercaptoethanol, 500 uM each of dATP, dGTP, dCTP and dTTP, 5 ug of oligo-dT (phosphorylated and average size of 12–18) as primer, 50 uCi of $^{32}$PdCTP (3000 Ci/mmole) and 20 units of the ribonuclease inhibitor RNAsin. The reaction was initiated by addition of 100 units of reverse transcriptase and incubated for 30 minutes at 42° C. The reaction was stopped by addition of EDTA to 40 mM and the RNA was degraded by incubation for 20 min. at 65° C. in 0.2M NaOH. The base was neutralized by addition of 20 ul 2M Tris, pH 7.4. The reaction mix was then extracted with phenol/chloroform, and back extracted with 50 ul TE. The aqueous phases were pooled and passed over a 1 ml sephadex G-50 column. The excluded fraction containing the first strand cDNA was recovered and ethanol precipitated. The first strand cDNA was converted to double stranded cDN by incubation for 12 hours at 16° C. with 40 units of the Klenow fragment of DNA polymerase I in a 100 ul reaction containing 50mM potassium phosphate, pH 7.4, 2.3 mM DTT, 2-mercaptoethanol, 10mM MgCl$_2$, 250 uMolar each of the 4 deoxynucleotide triphosphates and 25 uCi $^{32}$PdCTP. The reaction was stopped by extraction with phenol/chloroform and the unincorporated triphosphates were removed by passing the aqueous phase over a 1 ml Sephadex G-50 column. The excluded fractions were pooled and ethanol precipitated.

The cDNA pellet was washed with cold ethanol then resuspended in 200 ul of 100 mM Tris, pH 8, 5 mM EDTA, 80 uMolar S-adenosyl-Methionine. The methylase reaction was incubated with 300 units of EcoRl methylase for 60 minutes at 37° C. The reaction was stopped by extraction with phenol/chloroform and the methylated cDNA was collected by ethanol precipitation.

The cDNA pellet was rinsed with 70% ethanol then resuspended in 200 ul S1 buffer (Maniatis et al 1982), supra and incubated with 200 units of Sl-nuclease at 30° C. for 30 minutes. The reaction was stopped by extraction with phenol/chloroform and the cDNA collected by ethanol precipitation.

The double stranded cDNA was blunted by incubation in 100 ul of 20 mM Tris, pH 7.4, 50 mM NaCl, 10 mM 2 mercaptoethanol and 500 uMolar of dGTP, dCTP, dTTP and dATP with 25 units of Klenow at room temperature for 30 minutes. The reaction was stopped by extraction with phenol/chloroform and the cDNA collected by ethanol precipitation.

The cDNA was ligated in 50 ul of T4 ligase buffer (Maniatis et al 1982), supra with 500 pMoles of EcoRl linkers purchased from New England Biolabs (sequence: pCGGAATTCCG) using 2000 units of T4 ligase overnight at 16° C. The reaction was stopped by incubation at 70° for 20 minutes then diluted to 300 ul such that the final salt concentration was 0.1 M NaCl, 10 mM MgCl$_2$, 50 mM Tris-Cl pH 7.4. The cDNA was then digested for 120 minutes at 37° with 700 units of EcoRl. The reaction was stopped by extraction with phenol/chloroform and the cDNA collected by ethanol precipitation. The pellet was resuspended in 50 ul of TE and passed over a 5 ml Cl-4B column. The excluded fractions were pooled and ethanol precipitated. The precipitated cDNA was electrophoresed through a 1% agarose gel in Tris acetate buffer in the presence of 1 ug/ml ethidium bromide. cDNA in the size range 500-4000 base pairs was isolated from the gel using the standard glass powder procedure. The eluted cDNA was extracted with phenol/chloroform, ethanol precipitated and the pellet (after an ethanol rinse) was resuspended in 50 ul of TE. The final yield was 100-500 ng.

The expression vector p91023(B) was digested to completion with EcoRl, phosphatase treated, fractionated on 0.8% agarose gel and isolated by the standard glass powder procedure. The vector (400ng) was then ligated with 100 ng of cDNA in a 100 ul reaction (standard T4 ligase reaction) overnight at 16° C. The reaction was stopped by extracting with phenol/chloroform then the ligated cDNA was collected by ethanol precipitation after adding 5 ug of tRNA as carrier.

The ethanol precipitated DNA was rinsed with 70% ethanol then resuspended in 100 ul of TE. This DNA was used in 4 ul aliquots to transform E. coli MC1061 (4 ul in a 100 ul transformation). Each of the 25 transformations was spread onto a 150 mm petri dish with 1% agar, L-broth and 10 ug/ml tetracycline (Tet plate) and incubated overnight at 37°. Approximately 2000 colonies grew on each plate, resulting in a total of about 50,000-60,000 colonies. After reaching approximately 0.5 mm in diameter, the colonies were transferred to nitrocellulose disks (137 mm) by carefully placing a dry filter on the surface of the plate then smoothly peeling off the filter. All of the colonies on the plate were transferred to the filter which was then placed (colony side up) on a fresh Tet plate. After allowing the colonies to grow several hours, one replica was prepared from each of the filters by placing a fresh wetted filter exactly over the original filter, pressing them together, peeling them apart then returning each filter to a fresh Tet plate and incubating the plates overnight at 37°. Each replica was carefully marked such that it would be realigned with the original filter.

Step 5. Plasmid DNA Pool Preparation

Each of the 25 replica filters was carefully sectioned into eighths using a scalpel and noting the orientation of each eighth relative to the original master filter. The colonies were scraped from each section into 10 ml of L-Broth. The bacteria were collected by centrifugation (3000 RPM, 10 min., Beckman J-6 centrifuge), resuspended in 0.6 ml of 25% sucrose, 50 mM Tris-HCl pH 8.0, converted to protoplasts by addition of 0.12 ml of 5 mg/ml lysozyme, and incubated on ice for 5-10 min. The protoplasts were next incubated at room temperature for 10 min. following the addition of 0.125 ml of 0.5M EDTA then lysed by addition of 0.12 ml of 10% SDS in 50 mM Tris-HCl, pH 8.0. The lysate was mixed gently, incubated at room temperature for 15 min. then protein and chromosomal DNA were precipitated by the addition of 0.3 ml of 5M NaCl. After incubation on ice for 15 min., the lysate was centrifuged in an Eppendorf centrifuge for 30 min. in the cold. The supernatant was carefully removed leaving behind the viscous DNA/protein pellet and was diluted by the addition of 2.5 ml H$_2$O. The mixture was extracted with 1 ml of phenol, the layers separated by centrifugation (10K for 10 min. in the Sorvall SS-34 rotor) and the aqueous layer removed to a fresh tube. DNA was precipitated by adding 0.5 ml of 5M NaCl and 7.5 ml of cold ethanol and freezing the mixture several times in a dry ice ethanol bath. The precipitate was collected by centrifugation (10K, 15 min. in the Sorvall SS-34), resuspended in 0.3 ml of 0.3M sodium acetate, transferred to a 1.5 ml eppendorf tube and re-precipitated by the addition of 1 ml of ethanol. After 10-15 min. in a dry ice ethanol bath, the precipitated DNA was collected by centrifugation (5 min. in the Eppendorf centrifuge) and the final pellet wa resuspended in 100 ul of sterile TE (10 mM Tris pH8, 1 mM EDTA). From a typical preparation, 5-10 ug of plasmid DNA was obtained. Each preparation contained the DNA from 200-500 colonies on the original filter. A total of 200 DNA samples were prepared from the 25 filters.

Step 6. Isolating CSF Clone

Each of the DNA samples from Step 5 were separately transfected into M6 COS monkey cells as described below.

The M6 cells were grown routinely in DME (available from Gibco) plus 10% HIFCS in 90 mm plates, split twice a week at 1:6 dilution. Twenty-four hours after splitting 1:6 the M6 cells are ready for transfection. First, plates were aspirated and washed twice with 7 ml of serum-free DME. The DNA was dissolved in 10 mM Tris (pH 7.5) and 1 mM EDTA, and added to DME medium containing 2 mM glutamine, 100 ug/ml streptomycin, 100 U/ml penicillin and 0.25 mg/ml DEAE Dextran totalling 4 ml with the Tris-DNA solution. The 4 ml of medium containing dissolved DNA was added to the plate containing M6 COS cells and incubated for 12 hours.

After incubation, the cells were rinsed once or twice with 7 ml SF DME. Then, 5 ml of DME with 10% HIFCS, 100 u/ml penicillin, 100 ug/ml streptomycin, 2 mM glutamine, 0.1 mM chloroquin was added and the cells were incubated for 2½ hours.

After 2½ hours, the cells were rinsed once with SF DME and 10 ml DME +10% HIFCS/plate was added. After 30 hours, the media was removed and 4 ml of DME +10% HIFCS was added to each plate. The conditioned media were harvested after 24–26 hours of further incubation.

The conditioned medium from each transfection was assayed for CSF activity using the KG-1 assay. For each pool positive for CSF activity, as determined by assaying the conditioned medium from the COS cells, the clone on the original master filter having CSF DNA had to be identified. All of the bacterial colonies in the section used to make the DNA sample were picked from the original master filter. One pool DNA sample giving a positive test came from a section having 320 colonies, and each colony was picked into 3 ml of L-Broth +10 ug/ml tetracycline. The cultures were grown overnight. The 320 colonies were placed in an 18×18 matrix. Pools were prepared from each horizontal row and vertical column of the matrix (36 total pools) (note: the last horizontal row had only 14 clones). DNA samples were prepared from each pooled culture then used to transfect COS cells. The conditioned medium from these transfections were assayed using the KG-1 colony assay. Two positives were obtained from this set of transfections: one in a vertical column, the other a horizontal row. The culture common to these pools contained the CSF cDNA.

Twelve individual clones from this culture were isolated and DNA was prepared from 10 ml cultures in L-Broth as described above. 10 ul samples of DNA from these preparations were digested with EcoRl and the resulting DNA fragments were analyzed by agarose gel electrophoresis. Nine of the twelve clones had a common insert having approximately 750 base pairs. The DNAs from four of these clones and the remaining three clones were introduced into M6 COS cells as described above. The conditioned media from these transfections were assayed using the KG-1 assay as well as the bone marrow assay for CSF. The four clones which contained the 750 base pair fragment all directed the expression by the M6 COS cells of high levels of CSF activity as detected in either assay while the other three clones did not. Thus, the coding region for CSF must be located within the 750 base pair insert.

The DNA sequence coding for CSF was removed from the transformation vector of the positive clone by digestion with EcoRl, subcloned into M13 and sequenced using standard dideoxy sequencing methods. This sequence and the transformation vector p91023(B) containing it have been deposited with the American Type Culture Collection in a strain of *E. coli* - MC1061 under the deposit number ATCC 39754.

Step 7. Expression of CSF Protein

M6 COS monkey cells transformed with vector p91023(b) containing CSF/cDNA as isolated in Step 6 were grown as described in Step 6 to produce CSF protein in the culture medium.

Step 8. Purification of CSF Protein

Tissue culture medium containing CSF were loaded onto an octyl-Sepharose column in 1 M $(NH_4)_2SO_4$, 20 mM Tris, pH 7.4 and eluted in 30% ethanol, 20 mM Tris, pH 7.4. The eluate was chromatographed on Ultrogel AcA44 according to the standard conditions suggested by the manufacturer (LKB). Fractions containing CSF activity are run on reverse phase C4 HPLC (Vydac; Separations Group) using 0.1% trifluoroacetic acid in water-acetonitrile, followed by reverse phase C4 HPLC in 0.15% heptafluorobutryric acid in water-acetonitrile. The approximate specific activity on human bone marrow of protein thus prepared is:

$$\frac{(16 \text{ colonies} - 10 \text{ colony background}) \times 1295 \text{ fold dilution}}{0.01 \text{ ml} \times 0.002 \text{ mg/ml}} = X$$

$$X = 3.9 \times 10^8 \text{ colonies/mg}$$

This protein is active to a concentration of:

$$\frac{0.002 \text{ mg}}{\text{ml}} \times \frac{1}{3.88 \times 10^3 \text{ dilution}} \times \frac{1 \text{ mmole}}{20,000 \text{ mg}} = Y$$
(approximately)

$$Y = 2.6 \times 10^{-11} M$$

This invention has been described in detail, including the preferred embodiments thereof. However, it will be appreciated that those skilled in the art, upon consideration of this specification, may make modifications and improvements within the spirit and scope of the invention.

For instance, DNA from a genomic library may be used as the source of the desired gene for insertion into the transient expression vector. The transient expression vector may be expressed in vitro, i.e. without transfection or microinjection into cells. The transient expression vector may be inserted directly into mammalian or insert cells without first replicating in procaryotic cells. The gene being sought may be coding for a protein or factor that is not secreted—thus, the host cells may have to be lysed for detection of the protein or factor. All such and similar modifications are within the scope of the invention.

What is claimed:

1. A method for identifying a cDNA sequence encoding a desired protein, comprising the steps of:
    (a) preparing a cDNA library from a cell line that expresses the desired protein;
    (b) inserting said cDNA library into isolation expression vectors, said vectors having regulatory sequences capable of directing replication in bacterial cells and a promoter that directs replication and expression of said cDNA in predetermined mammalian cells;
    (c) inserting said vectors into a bacterial cells and culturing said bacterial cell to produce clones;
    (d) collecting pools of a predetermined number of colonies of said bacterial clones;
    (e) preparing DNA from each said pool by substantially removing bacterial contaminants therefrom, which inhibit expression of said DNA in mammalian cells;
    (f) transfecting the DNA from each pool into said mammalian cells;
    (g) culturing said transfected mammalian cells to produce mammalian cell cultures and testing media from each of said cell cultures for expression of the activity of the desired protein;

(h) selecting bacterial pools which correspond to the mammalian cell cultures expressing said activity;

(i) repeating steps (e) through (h) until a colony of the bacterial cells containing the cDNA that expresses the desired protein when introduced into mammalian cells is identified; and (j) excising the cDNA from the bacterial colony identified in step (i).

2. The method according to claim 1, wherein said mammalian cells are COS cells.

3. The method according to claim 1, wherein said protein is a secreted protein.

4. The method according to claim 1, wherein said protein has a molecular weight up to about 100,000 daltons.

5. The method according to claim 1, wherein said isolation expression vectors are selected from the group consisting of high copy number vectors and vectors amplifiable with chloramphenicol.

6. The method according to claim 1, wherein said isolation expression vector is p91023(B).

7. The method according to claim 1, wherein said cDNA encoding said protein contains about 4000 nucleotides.

8. The method according to claim 7, wherein said cDNA encoding said protein contains about 2000 nucleotides.

* * * * *